United States Patent [19]

Jacklich et al.

[11] Patent Number: 4,710,172

[45] Date of Patent: Dec. 1, 1987

[54] HIGH PRESSURE SYRINGE WITH PRESSURE INDICATOR

[75] Inventors: John Jacklich, 102 Western Ct., Santa Cruz, Calif. 95060; George Mikula, Bozeman, Mont.

[73] Assignee: John Jacklich, Santa Cruz, Calif.

[21] Appl. No.: 934,434

[22] Filed: Nov. 24, 1986

[51] Int. Cl.⁴ ............................................. A61M 1/00
[52] U.S. Cl. .................................... 604/118; 604/209; 604/224
[58] Field of Search ............... 604/118, 121, 207, 208, 604/209, 224

[56] References Cited

U.S. PATENT DOCUMENTS 4,623,335  11/1986  Jackson .............................. 604/118
4,624,659  11/1986  Goldberg et al. ................... 604/121

FOREIGN PATENT DOCUMENTS 0080793  6/1983  European Pat. Off. ............ 604/224

Primary Examiner—John D. Yasko

[57] ABSTRACT

A high pressure anesthetic syringe is provided for use in procedures such as intraligamentary anesthesia wherein a high pressure is generated by a drive mechanism to advance a piston rod in a direction to express liquid anesthesia from a glass carpule, wherein a pressure indicating mechanism is provided by including an elongated stem slidably mounted within the piston rod of the syringe and wherein pressure applied to the liquid anesthetic is indicated by relative movement between the elongated stem and the piston rod.

10 Claims, 3 Drawing Figures

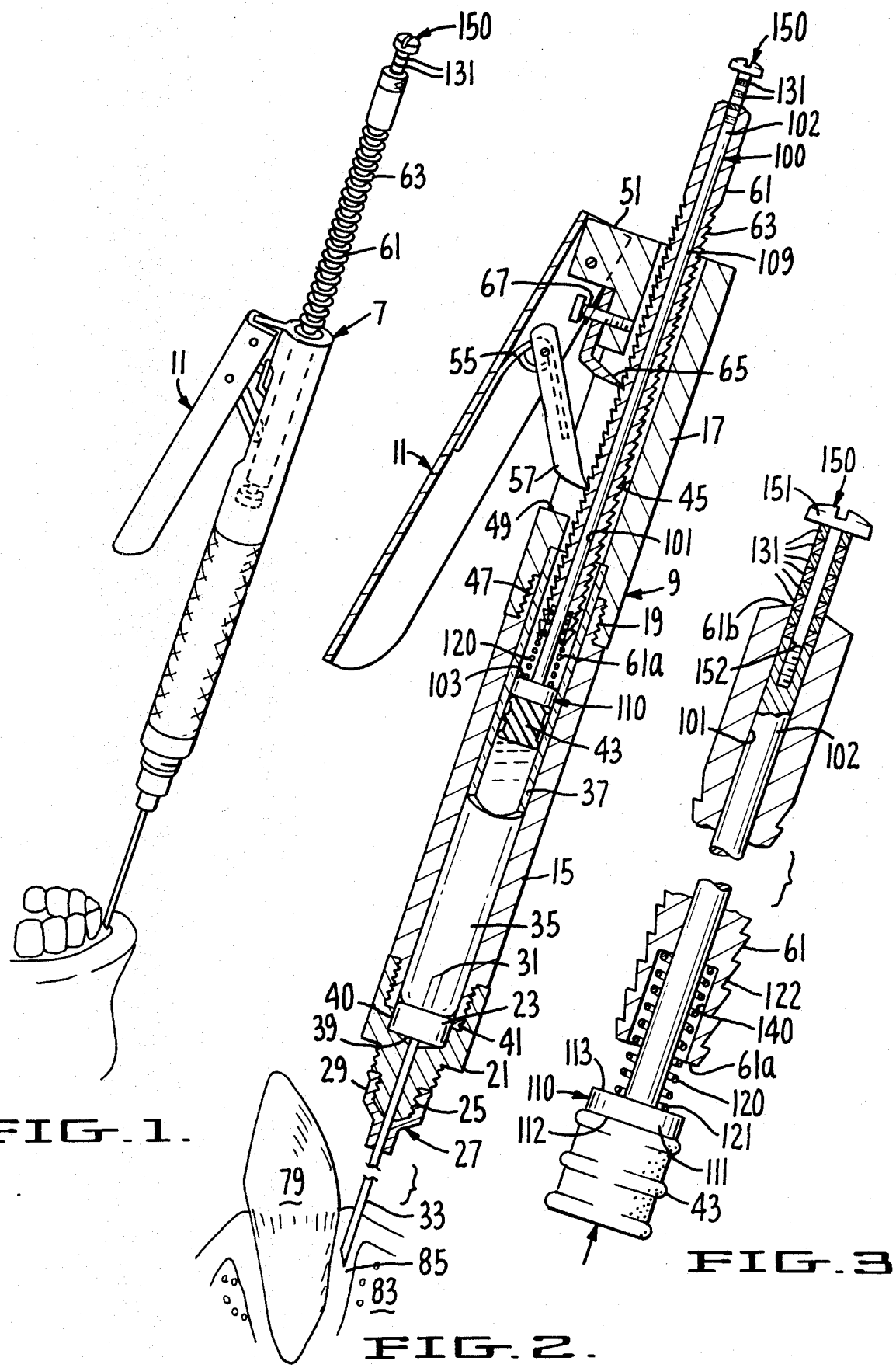

HIGH PRESSURE SYRINGE WITH PRESSURE INDICATOR

CROSS-REFERENCE TO RELATED APPLICATION

This application is an improvement to the syringe shown in U.S. Pat. No. 4,444,560. The improvement of the present invention can also be used with prior art "pistol grip" type syringes.

SUMMARY OF THE INVENTION

The present invention relates to a pressure indicating mechanism that may be utilized in conjunction with high pressure syringes in general. One particular use of the mechanism is in conjunction with high pressure injections into the dental periodontal ligament.

A primary object of the invention is to provide a high pressure syringe with a pressure indicating mechanism which allows the practitioner to apply a predetermined amount of pressure to the anesthetic or other solution being injected into the patient.

A further object of the invention is to provide a high pressure dental syringe with a pressure indicating mechanism wherein the practitioner may apply different levels of pressure to enhance various procedures and to facilitate the use of an optimal pressure to account for variations of optimal pressure because of the differences in patients, procedures and the tooth or teeth being worked on.

Still another object of the invention is to allow the practitioner to readily ascertain the amount of pressure being applied and to ascertain immediately if excess pressure is being applied so that preventive measures may be taken to avoid carpule breakage or to avoid a sudden high pressure burst of anesthetic or other solution into the patient.

Another object of the present invention is to provide a pressure indicating mechanism for use in high pressure medical syringes which will reduce the incidence of carpule breakage.

A further object is to provide a pressure indicating mechanism that prominently displays the pressure when viewed from virtually any direction.

Another object is to provide an indicating mechanism which utilizes a plurality of colored rings, which withstand the cleansing chemicals and various methods of sterilization.

Other features and advantages of the invention will be brought out in the balance of the specification.

BRIEF DESCRIPTION OF THE DRAWINGS

FIG. 1 is a perspective view showing an instrument embodying the present invention in use;

FIG. 2 is an enlarged view of the instrument, partly in section, showing it in use; and FIG. 3 is a sectional view of a portion of the instrument incorporating an alternate embodiment.

DESCRIPTION OF THE PREFERRED EMBODIMENTS

Referring to the drawings by reference characters, the device of the present invention is generally designated 7 and, as best shown in FIG. 2, consists of a central tubular portion 9 and an operating handle 11. In FIG. 1 the device is shown in relation to a patient's jaw.

The tubular portion 9 consists of a lower cylinder or body part 15 and an upper cylinder or body part 17 connected together by means of threads 19.

At the distal end of the cylinder or body part is a nosepiece 21 which has internal threads 23 for attaching it to the lower cylinder body part 15 and second set of threads 25 which may be used for attaching it to a double cannula assembly 27. The cannula assembly 27 includes a hub 29 with internal threads to mate with the threads 25 to support the double ended cannula which has a short end 31 adapted to extend into the nosepiece 21 and to pierce the lower diaphragm 39 of carpule 35. Cannula 27 also has a longer external end 33 which is used for the actual injection of the medicine. As shown in FIG. 2, the cannula or needles 33 is shown in the periodontal ligament 85 which is the ligament between tooth 79 and the supporting jawbone 83.

The device of the present invention is adapted for use with a carpule 35 which consists of a glass cylinder 37, a fixed end portion shown generally as 40 which consists of a metal shoulder 41 and a diaphragm 39 adapted to be penetrated by the short end 31 of cannula 27. At the opposite end is a resilient bung 43 which can be pushed into the cylinder 37 to discharge a medication contained therein.

The upper portion or body part 17 is generally round on the outside with a central passage 45 and with threads 47 to mate with threads 19. Part 17 has a slot 49 at one side thereof and also has a lug 51 which extends outwardly just above the slot and the operating handle 11 is pivoted on this lug. A spring 55 normally biases the handle 11 outwardly. A ratchet 57 is provided on handle 11 and the same spring 55 biases ratchet 57 into the slot or groove 49 as is best shown in FIG. 2.

A piston rod 61 extends into the opening 45 and the piston rod has a number of ratchet teeth 63. Ratchet teeth 63 may either form a thread or may be a plurality of rings as shown in FIG. 1. A pawl 65 is urged by spring 67 into contact with the ratchet teeth. As the handle 11 is worked back and forth, piston rod 61 will advance into the cylinder and pawl 65 will prevent return motion.

An elongated stem means 100 is provided which is slidably mounted within an elongated passageway 101 formed in piston rod 61. In the embodiment shown, stem means 100 comprises an elongated cylindrical, solid metal shaft 109 with an overall length greater than the length of piston rod 61.

Head means 110 is carried by the distal end 103 of stem means 100, head means 110 being adapted to engage the bung 43 of carpule 35. Head means 110 comprises a disc 111 with a diameter slightly less (i.e. 0.005" to 0.010") than the inner diameter of carpule 35. Disc 111 has a flat distal surface 112 and a flat proximal surface 113, although distal surface 112 may be concave.

Spring means 120 is located between head means 110 and the distal end 61a of piston rod 61.

Indicator means 130 comprises a plurality of colored, anodized aluminum rings 131 carried on the proximal end 102 of stem means 100. Indicator means 130 is actuated by relative motion between elongated stem means 100 and piston rod 61, so that the pressure being applied to the anesthetic in carpule 35 is displayed for use by the operator of the syringe. Indicator means 130 may be viewed from virtually any direction by the user.

FIG. 3 shows an alternate embodiment wherein spring means 120 at one end 121 seats against head means 110 and the other end 122 of spring means 120 is carried in a recess 140 formed in the distal end 61a of piston rod 61.

Cap means 150 comprises screw 151 which threads into recess 152 formed in the proximal end 102 of stem means 100. Cap means 150 prevents the proximal end 102 of stem means 100 from going past proximal end 61b of piston rod 61 and entering passageway 101. Cap means 150 also provides a means for preloading spring means 120, so that when cap means 150 is seated against the proximal end 61b of piston rod 61, spring means 120 may be partially compressed.

The plurality of rings 131 perform the pressure indication function. As shown, eight separate rings are slid onto screw 151 prior to screw 151 being threaded onto stem means 100. The rings are anodized aluminum and will effectively resist various cleansing and sterilizing agents without becoming discolored. The color of the rings may be arranged in any predetermined pattern. Each ring may be a different color, or every other ring may be a neutral, background color. The thicknesses of the rings may also vary.

Cap means 150 is removable from stem means 100 to facilitate cleaning and changing of spring means 120 and rings 131.

In operation, the user separates the body parts 15 and 17, and inserts carpule 35 into body part 15. Piston rod 61 is reset by pulling it forwardly through body part 17, and by inserting head means 110 and piston rod 61 into the upper end of passage 45, and advancing piston rod 61 until ratchet 57 is in engagement with ratchet teeth 63. The upper body part 17 is threaded onto body part 15, double cannula 27 is threaded into place and the syringe is ready for use.

In the embodiment shown in FIGS. 1-3, the syringe may be utilized with a fourth finger or thumb rest, nearly completely concealed in the hand, and the operating lever may be actuated by the user's thumb or fingers, depending on how the syringe is held. As the anesthetic (or other medication) is being injected, indicator means 130 displays prominently, and from virtually any viewing angle, the pressure being applied to the anesthetic.

What is claimed is:

1. In a syringe capable of delivering anesthetic under high pressure for use in procedures such as intraligamentary anesthesia, wherein said syringe has a barrel for holding an anesthetic carpule, said carpule having a bung at a first end of the carpule which may be driven toward the second end of the carpule, the second end having a diaphragm which is adapted to be pierced by one end of a double cannula, a piston rod for actuating the carpule bung, and a drive mechanism for advancing said piston rod to express the anesthetic from said carpule, the improvement comprising:
   a. elongated stem means slidably mounted within a passageway formed in said piston rod,
   b. head means carried at one end of said elongated stem means, said head means adapted to engage the bung of said carpule,
   c. spring means located between said head means and said piston rod, and
   d. indicator means actuated by relative motion between said elongated stem means and said piston rod, whereby the pressure being applied to said anesthetic is displayed for use by the operator of said syringe.

2. The syringe of claim 1 wherein said indicator means comprises a plurality of colored rings carried by said elongated stem means, whereby the applied pressure is displayed prominently for viewing from virtually any direction.

3. The syringe of claim 2 further comprising removable cap means attached to the proximal end of said stem means to facilitate preloading of said spring means.

4. The syringe of claim 3 wherein said cap means comprises a screw which carries said plurality of colored rings.

5. The syringe of claim 1 wherein said piston rod has a recess formed in its distal end and said spring means extends from said head means into said recess.

6. A high pressure dental syringe comprising in combination:
   a. an elongated cylindrical chamber for receiving a carpule containing a medication, said carpule having a bung which may be driven to express anesthetic from the carpule, said elongated cylindrical chamber having two separable main body parts, each body part having connecting means at one end thereof for positively securing the two parts together after said carpule has been inserted into one of said two parts;
   b. actuating means arranged so that the elongated cylindrical chamber can be held in the palm of a user's hand and be operated by the user's thumb and/or fingers including an operating handle pivotably mounted on the other of said two parts of said cylinder, the free end of said operating handle directed towards the area of said connecting means for said two parts of said cylindrical chamber and being biased outwardly to a first position at an acute angle to said chamber and being movable to a second position parallel to said chamber;
   c. an elongated piston rod movable within said chamber, said piston rod having a plurality of ratchet teeth thereon;
   d. a ratchet pivoted to said operating handle and extending into said chamber in operative relationship to engage said ratchet teeth and to force said piston rod toward the distal end of said cylindrical chamber;
   e. means biased into said ratchet teeth to permit said piston rod to move in said cylindrical chamber for exerting force on said carpule but to prevent reverse motion of said piston rod and thus release of the force on said carpule;
   f. elongated stem means slidably mounted within a passageway formed in said piston rod;
   g. head means carried at one end of said elongated stem means, said head means adapted to engage the bung of said carpule;
   h. spring means located between said head means and said piston rod, and
   i. indicator means actuated by relative motion between said elongated stem means and said piston rod, whereby the pressure being applied to said anesthetic is displayed for use by the operator of said syringe.

7. The syringe of claim 6 wherein said indicator means comprises a plurality of colored rings carried by said elongated stem means, whereby the applied pressure is displayed prominently for viewing from virtually any direction.

8. The syringe of claim 7 further comprising removable cap means attached to the proximal end of said stem means to facilitate preloading of said spring means.

9. The syringe of claim 8 wherein said cap means comprises a screw which carries said plurality of colored rings.

10. The syringe of claim 6 wherein said piston rod has a recess formed in its distal end and said spring means extends from said head means into said recess.

* * * * *